(12) United States Patent
Boyes et al.

(10) Patent No.: US 10,078,081 B2
(45) Date of Patent: Sep. 18, 2018

(54) ISOTOPICALLY LABELED GLYCANS AND METHODS FOR PRODUCING THE SAME

(71) Applicant: GlycoScientific LLC, Athens, GA (US)

(72) Inventors: Barry Edward Boyes, Wilmington, DE (US); Ronald C. Orlando, Athens, GA (US)

(73) Assignee: GlycoScientific LLC, Athens, GA (US)

( * ) Notice: Subject to any disclaimer, the term of this patent is extended or adjusted under 35 U.S.C. 154(b) by 49 days.

(21) Appl. No.: 14/638,807

(22) Filed: Mar. 4, 2015

(65) Prior Publication Data
US 2015/0253332 A1    Sep. 10, 2015

Related U.S. Application Data

(60) Provisional application No. 61/948,165, filed on Mar. 5, 2014.

(51) Int. Cl.
C12Q 1/44     (2006.01)
G01N 33/58    (2006.01)

(52) U.S. Cl.
CPC ..... *G01N 33/58* (2013.01); *G01N 2333/4722* (2013.01); *G01N 2400/10* (2013.01); *G01N 2458/15* (2013.01); *G01N 2560/00* (2013.01); *Y10T 436/143333* (2015.01)

(58) Field of Classification Search
None
See application file for complete search history.

(56) References Cited

U.S. PATENT DOCUMENTS

2006/0099674 A1    5/2006   Alliger et al.
2010/0297609 A1*  11/2010   Wells ............... G01N 33/502
                                                        435/5
2011/0053216 A1    3/2011   Vermaas
2011/0065603 A1*   3/2011   Ripoll ............... G01N 23/2258
                                                        506/9
2012/0264688 A1   10/2012   Hinderer et al.

FOREIGN PATENT DOCUMENTS

WO    2013/079558    6/2013

OTHER PUBLICATIONS

Nelson et al., Mol. Path. 53: 111-117 (2000).*
Suzuki et al., Anal. Biochem. 347: 324-326 (2005).*
Wada et al., 2007, "Comparison of the methods for profiling glycoprotein glycans—HUPO Human Disease Glycomics/Proteome Initiative multi-institutional study," Glycobiology, 17(4):411-422.

* cited by examiner

*Primary Examiner* — Erin M. Bowers
(74) *Attorney, Agent, or Firm* — Riverside Law LLP

(57) ABSTRACT

The present invention relates to methods for creating isotopically-labeled glycans or glycoconjugates for use in the analysis of glycans, and compositions produced from such methods. The present invention also relates to the use of isotopically labeled glycans or glycoconjugates as standards in glycan identification and/or quantification methods. In one embodiment, the method of the present invention can be used to accurately determine the levels of glycans in a sample based upon the addition of a known quantity of a standard comprising isotopically-labeled glycans to the sample prior to analysis. In one embodiment, the present invention relates to a composition for an analytical standard comprising one or more isotopically-labeled glycans or glycoconjugates.

11 Claims, 5 Drawing Sheets

ISOTOPICALLY LABELED GLYCANS AND METHODS FOR PRODUCING THE SAME

CROSS-REFERENCE TO RELATED APPLICATIONS

This application claims priority to U.S. Patent Application Ser. No. 61/948,165, filed Mar. 5, 2014, the entire contents of which are incorporated herein by reference.

BACKGROUND OF THE INVENTION

There are several potential techniques for incorporating an isotope into a glycan. One method is to grow the cell or organism on a labeled material so that the isotope is included into all potential labeling sites in a cell, i.e., whole cell labeling. For instance, it is known in the art that mice grown on food that only contains $^{15}N$ will result in all of the nitrogen in these mice being the isotopic variant, including the nitrogen in the sugars. Another similar approach is to grow cells/organisms with $^{13}C$-labeled glucose as its sole energy source. This has been done previously in the art with yeast, resulting in very high levels of isotope incorporation (Rampler et al., "Production of a $^{13}C$-labeled Internal Standard for Quantitative Glycomics," proceedings of the 61st ASMS Conference on Mass Spectrometry, Minneapolis, Minn., June 2013).

However, whole-cell labeling is undesirable because it is expensive and the labeled glycans may not be of the correct type. In any type of isotopic labeling, the isotope is typically the most expensive reagent used in the technique, and in whole-cell labeling, the isotope goes into all molecules, not only glycans. Further, the most useful type of analytical standard contains molecules that are similar to, if not nearly identical to, the compound to be analyzed. In whole-cell labeling, the $^{15}N$ mice and $^{13}C$ yeast have different glycans than the glycans present in a recombinant IgG, for example. Thus, the advantage of using an isotopically labeled internal standard is lost.

Another potential method for isotopic glycan labeling is the use of isotopically-labeled nucleotide-sugars. An isotopic variant of a nucleotide sugar can be added to the cell culture media, e.g., UDP-GalNAc with the isotope label in the GalNAc. However, this approach is undesirable for several reasons: 1) Unlabeled nucleotide sugar would be present because they are continually biosynthesized by the cell, and consequently the extent of labeling is generally poor; 2) Nucleotide sugars are highly energetic and thus have short lifetimes in solutions, therefore, they would most likely need to be continually added to the media; 3) A mechanism for cells to incorporate nucleotide sugars into the cell where they are needed for glycoprotein biosynthesis is not readily available; and 4) Nucleotide sugars are difficult to obtain or synthesize. Accordingly, the use of isotopically-labeled nucleotide-sugars is not commercially viable.

Another potential method for the isotopic labeling of a glycan is by in vivo introduction of an isotope into a nucleotide sugar. To understand this method for incorporating isotopes into glycoprotein chains, the in vivo biosynthetic pathway of glycoprotein glycans must first be considered. The glycans attached to proteins are created by the sequential addition of multiple monosaccharides to either existing glycans (either N- or O-linked) or to the dolichol phosphate precursor for N-linked glycan chains. These monosaccharide additions are performed enzymatically, which controls the site of addition, and utilizes an activated nucleotide sugar as the source of the monosaccharide. For example, a glycosyltransferase would transfer a glucose residue from uracil-diphosphate glucose (UDP-glucose) to the glycan chain. Consequently, the addition of each different monosaccharide requires different transferases and different nucleotide sugars (UDP-GalNAc, GDP-Man, CMP-NeuAc, etc.)

Methods of isotopically labeling glycans via in vivo introduction of an isotope into a nucleotide sugar have been identified in the art for the purposes of identifying and/or quantifying glycans in a glycoprotein sample. For example, Wells et al. (U.S. Patent App. Pub. No. 2010/0297609, which is incorporated by reference herein in its entirety) describes a method of isotopically labeling glycans with $^{15}N$ in cell culture for performing relative quantitative glycomics. The method described in Wells, termed isotopic detection of aminosugars with glutamine (IDAWG), relies on the hexosamine biosynthetic pathway that uses the side-chain of glutamine as the donor source of nitrogen for aminosugars in the production of sugar nucleotides. The IDAWG method is based on the introduction of $^{15}N$-glutamine into otherwise glutamine-free media to cause all aminosugars in cells or tissues grown in the media to become labeled, i.e., increased in mass by 1 dalton. The labeled cells or tissues can then be compared to control cells or tissues grown in $^{14}N$-glutamine media to perform glycan detection and/or quantification.

However, current methods of identifying and/or quantifying glycoprotein glycans, such as IDAWG, are associated with a level of error that is unacceptable for most applications. The average error associated with such methods has been found to be over 100% (Wada et al., 2007, Glycobiology, 17(4):411-422; Orlando et al., 2010, J Biomol Tech, 21(3 Suppl): S17-S18). This level of uncertainty is unacceptable for most, if not all, applications where glycans are desired to be identified and/or quantified. For example, a method with this level of uncertainty could not be used in applications needing FDA approval, such as the characterization of therapeutic agents.

In addition to the currently known glycan identification methods being associated with a high level of error, these methods are limited in potential end-use applications. For example, the IDAWG method is only useful for whole glycomic experiments, i.e., comparing one cell line to another cell line. Specifically, the IDAWG method involves the steps of growing a first cell line in a $^{15}N$-glutamine medium that is otherwise glutamine-free, while growing a second cell line, or control line, in a $^{14}N$-glutamine medium. The first cell line can be manipulated in some manner during growth, for example by treating the cell line with one or more chemicals or by varying environmental conditions, and the effects of the manipulation can be determined by comparing the isolated glycoconjugates or glycans from the first cell line to the isolated glycoconjugates or glycans from the control cell line via mass spectrometry.

However, the labeling techniques in the IDAWG method cannot generally be used to create a standard comprising glycans or glycoconjugates that can be used to analyze a sample from a different cell line because the extent of isotopic labeling by the IDAWG method is typically not high enough to provide accurate quantification of glycans outside of a direct comparison of two cell lines. Accordingly, the IDAWG method is only useful for a relative, but not absolute, analysis of glycans.

Thus, there is a continuing need for new and/or improved methods of isotopically labeling glycans, and for new methods of identifying and quantifying glycans. In addition, there is a need in the art for producing isotopically labeled glycans or glycoproteins for use as an analytical reference standard. The present invention addresses these continuing needs in the art.

SUMMARY OF INVENTION

The present invention relates to methods for isotopically labeling glycans and glycoconjugates, and the compositions produced by such methods. In one embodiment, the present invention is a method for making a standard for the quantification or identification of glycans in a sample, comprising the steps of: culturing a sample in a culture medium, wherein said culture medium comprises $^{15}$N-glutamine and a $^{15}$N-ammonium source, thereby producing $^{15}$N-labeled glycoconjugates and/or $^{15}$N-labeled glycans, i.e., free $^{15}$N-labeled glycans. The method of the present invention can comprise additional steps, such as isolating at least one $^{15}$N-labeled glycoconjugate or glycan from said culture medium, or releasing at least one $^{15}$N-labeled glycan from said at least one $^{15}$N-labeled glycoconjugate.

In another embodiment, the method of the present invention is a method for quantifying or identifying at least one glycan in a sample, comprising the steps of: providing a sample comprising analyte glycoconjugates; mixing a pre-determined quantity of a $^{15}$N-labeled glycoconjugate standard with said analyte glycoconjugates to form a glycoconjugate mixture; releasing glycans from said glycoconjugate mixture to form a glycan mixture, wherein said glycan mixture comprises analyte glycans and $^{15}$N-labeled glycans; measuring a mass spectrum of said glycan mixture; and determining the presence and/or quantity of at least one glycan in the sample by comparing a peak in the mass spectrum corresponding to at least one analyte glycan to a peak in the mass spectrum corresponding to a $^{15}$N-labeled glycan. In yet another embodiment, the method of the present invention is a method for identifying or quantifying at least one glycan in a sample, comprising the steps of: providing a sample comprising analyte glycoconjugates; releasing glycans from said analyte glycoconjugates to form analyte glycans; mixing a pre-determined quantity of a $^{15}$N-labeled glycan standard with said analyte glycans to form a glycan mixture; measuring a mass spectrum of said glycan mixture; and determining the presence and/or quantity of at least one glycan in the sample by comparing a peak in the mass spectrum corresponding to at least one analyte glycan to a peak in the mass spectrum corresponding to a $^{15}$N-labeled glycan.

In one embodiment, the present invention is a method for determining the effect of a modulator on a sample, comprising the steps of: culturing a sample in a medium, thereby producing control glycoconjugates; removing a portion of said control glycoconjugates from said medium; applying a modulator to the sample remaining in said medium, thereby producing analyte glycoconjugates; mixing a pre-determined quantity of a $^{15}$N-labeled glycoconjugate standard with said control glycoconjugates to form a control glycoconjugate mixture; mixing a pre-determined quantity of a $^{15}$N-labeled glycoconjugate standard with said analyte glycoconjugates to form an analyte glycoconjugate mixture; releasing glycans from said control glycoconjugate mixture to form a control glycan mixture, wherein said control glycan mixture comprises control glycans and $^{15}$N-labeled glycans; releasing glycans from said analyte glycoconjugate mixture to form an analyte glycan mixture, wherein said analyte glycan mixture comprises analyte glycans and $^{15}$N-labeled glycans; measuring a mass spectrum of said control glycan mixture; measuring a mass spectrum of said analyte glycan mixture; and comparing the mass spectrum of said control glycan mixture to the mass spectrum of said analyte glycan mixture to determine the effect of the modulator on the sample.

In another embodiment, the method of the present invention is a method for determining the effect of a modulator on a sample, comprising the steps of: culturing a sample in a medium, thereby producing control glycoconjugates; removing a portion of said control glycoconjugates from said medium; releasing control glycans from said control glycoconjugates; applying a modulator to the sample remaining in said medium, thereby producing analyte glycoconjugates; releasing analyte glycans from said analyte glycoconjugates; mixing a pre-determined quantity of a $^{15}$N-labeled glycan standard with said control glycans to form a control glycan mixture; mixing a pre-determined quantity of a $^{15}$N-labeled glycan standard with said analyte glycans to form an analyte glycan mixture; measuring a mass spectrum of said control glycan mixture; measuring a mass spectrum of said analyte glycan mixture; and comparing the mass spectrum of said control glycan mixture to the mass spectrum of said analyte glycan mixture to determine the effect of modulation on the sample.

In one embodiment, the modulator is a compound of interest, such as a pharmaceutical compound, a protein, or a suspected toxin. In one embodiment, the step of applying a modulator to the sample remaining in said medium comprises exposing the sample to a microbe. In another embodiment, the step of applying a modulator to the sample remaining in said medium comprises exposing the sample to a change in an environmental condition. In yet another embodiment, the step of applying a modulator to the sample remaining in said medium comprises exposing the sample to radiation.

The present invention also relates to compositions. In one embodiment, the composition is a standard for use in the analysis of glycans in a sample, comprising at least one $^{15}$N-labeled glycoconjugate produced by a method of the present invention. In another embodiment, the composition is a standard for use in the analysis of glycans in a sample, comprising at least one $^{15}$N-labeled glycan produced by a method of the present invention. In another embodiment, the composition is a standard for use in the analysis of glycans in a sample, comprising at least one $^{15}$N-labeled glycoconjugate, wherein the degree of $^{15}$N-labeling of said at least one glycoconjugate is at least 95%. In yet another embodiment, the composition is standard for use in the analysis of glycans in a sample, comprising at least one $^{15}$N-labeled glycan, wherein the degree of $^{15}$N-labeling of said glycan is at least 95%.

In one embodiment, the $^{15}$N-labeled glycoconjugate in the method or composition of the present invention is a $^{15}$N-labeled glycoprotein, $^{15}$N-labeled glycolipid, or $^{15}$N-labeled proteoglycan. In one embodiment, the $^{15}$N-labeled glycoconjugate is selected from the group consisting of a $^{15}$N-labeled monoclonal antibody (mAb), fusion protein, hormone, cytokine, clotting factor, enzyme inhibitor, and/or enzyme. In one embodiment, the $^{15}$N-labeled glycan is attached to a glycoprotein selected from the group consisting of a monoclonal antibody (mAb), fusion protein, hormone, cytokine, clotting factor, enzyme inhibitor, and/or enzyme. In one embodiment, the $^{15}$N-labeled glycan is attached to erythropoietin (EPO).

In one embodiment, the $^{15}$N-ammonium source is $^{15}$N-ammonium chloride. In one embodiment, the culture medium is a serum-free medium. In one embodiment, the degree of labeling of the $^{15}$N-labeled glycoconjugate or glycan in the method or composition of the present invention is in the range of about 80-100%. In another embodiment, the degree of labeling of the $^{15}$N-labeled glycoconjugate or glycan is at least 90%. In yet another embodiment, the degree of labeling of the $^{15}$N-labeled glycoconjugate or glycan is at least 95%.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

Figure 1:
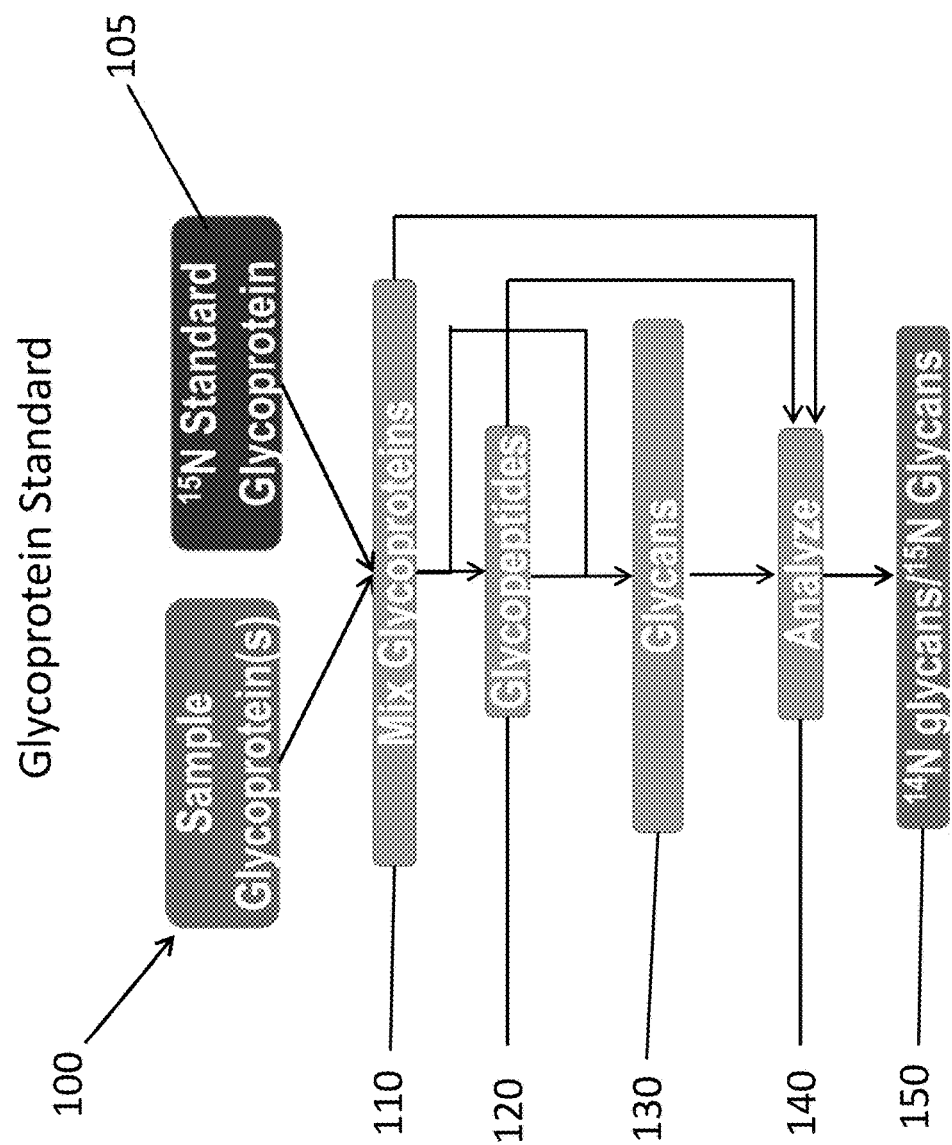
FIG. 1 is a schematic diagram of an exemplary embodiment of the method of the present invention for identifying and/or quantifying glycans, using a $^{15}$N-labeled glycoprotein as a reference standard.

It is to be understood that the figures and descriptions of the present invention have been simplified to illustrate elements that are relevant for a clear understanding of the present invention, while eliminating, for the purpose of clarity, many other elements found in the art related to glycans, glycoconjugates, glycosylation, glycomics, and the like. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods, materials and components similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate.

The term "standard" is used throughout this disclosure, and refers to any well-characterized composition that can be used in the analysis of an unknown or uncharacterized material. In various embodiments, the term "standard" can refer to any type of standard known to a person skilled in the art, including, but not limited to: an "internal standard," a "reference standard," an "analytical standard," and the like.

The terms "sample," "analyte," and the like are used interchangeably herein and refer to any substance, material, or composition that can be analyzed using the methods and compositions of the present invention. Types of samples that can be analyzed using the methods and compositions of the present invention include, but are not limited to isolated glycoproteins, proteoglycans, complex carbohydrates, an extract from an organism, or an organ or fraction thereof. Thus, the method of the present invention can be applied to the characterization and identification of the components of a mixture, or for the control and definition of in-process materials.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Description

The present invention relates to methods for creating an isotopically-labeled glycoprotein for use as a standard for the analysis of glycans, and compositions produced from such methods. In one embodiment, the method of the present invention can be used to accurately determine the levels of glycans in a sample based upon the addition of a known quantity of a standard comprising isotopically-labeled glycans to the sample prior to analysis. In one embodiment, the present invention relates to a composition for an analytical standard comprising one or more isotopically-labeled glycans or glycoconjugates. In a preferred embodiment, the one or more glycans or glycoconjugates are labeled with $^{15}$N.

The present invention also relates to the use of isotopically labeled glycans or glycoconjugates as standards in glycan identification and/or quantification methods. In one embodiment, the use of these standards results in an error level of 10% or less for glycan quantification, as opposed to error levels of over 100% for other methods of glycan quantification, such as IDAWG. An error level of 10% or less enables the methods of the present invention to be used for purposes previously not available in the field of glycan quantification, for example, in highly regulated areas such as the pharmaceutical industry.

In various embodiments, the method of the present invention relates to the in vivo introduction of an isotope into a nucleotide sugar. The present invention is based on the understanding that all amino sugars are derived from glucosamine 6-phosphate, which is produced by the addition of an amine functional group to fructose 5-phosphate. Generally, in the dominant pathway, the amino group is transferred from the amide group of glutamine or from free ammonia. The transfer of the amino group appears to be related to the relative expression level of the two enzymes responsible for this step, glucosamine-6-phosphate isomerase (or deaminase) 1 and 2. Consequently, the addition of glutamine with a $^{15}$N-labeled sidechain and/or $^{15}$N ammonia to the growth medium leads to the selective incorporation of an isotope into an activated sugar, which is the precursor of all nucleotide-amino sugars (e.g., GalNac, GlcNAc, NeuAc, NeuGC, etc.).

Accordingly, the methods and compositions of the present invention relate to the discovery that by using $^{15}$N-ammonia in combination with $^{15}$N glutamine, glycans with very high isotope specific incorporation can be produced. The methods of the present invention can produce glycans with a much higher degree of isotope labeling, for example glycans with >95% isotopic labeling, than currently known methods. Further, the methods of the present invention are relatively inexpensive because the isotope is targeted directly to the sugar. Therefore, in one embodiment, the composition of the present invention is substantially isotope-free in all locations aside from glycans.

In one embodiment, the method of the present invention is a method for making an analytical standard for the quantification and/or identification of glycans in a sample. The method includes the step of culturing a sample, for example any type of cell or tissue, in a culture medium, wherein the culture medium comprises $^{15}$N-glutamine and a $^{15}$N-ammonium source. As discussed herein, the presence of $^{15}$N-ammonia in combination with $^{15}$N glutamine results in $^{15}$N-labeled glycoconjugates in the sample, wherein the level of $^{15}$N-labeling in the sample is much higher than can be produced using methods currently known in the art. In one embodiment, the $^{15}$N-ammonium source is $^{15}$N-ammonium chloride. In one embodiment, the culture medium can comprise compounds that will react to produce $^{15}$N-ammonia during the culturing step. However, the $^{15}$N-ammonium source can be any source of $^{15}$N-ammonium or $^{15}$N-ammonia as would be understood by a person skilled in the art.

In addition, the present invention relates to compositions comprising $^{15}$N-labeled glycoconjugates with a high degree of $^{15}$N-labeling. In one embodiment, the composition of the present invention comprises one or more $^{15}$N-labeled glycans. In another embodiment, the composition of the present invention comprises one or more $^{15}$N-labeled glycoconjugates, such as, but not limited to: glycoproteins, glycopeptides, glycolipids, and extracellular glycans. In one embodiment, the composition of the present invention can comprise any $^{15}$N-labeled glycan or glycoconjugate that is produced using the methods of the present invention described herein. In one embodiment, the degree of $^{15}$N-labeling of the compositions of the present invention is at least 80%. In another embodiment, the degree of $^{15}$N-labeling of the compositions of the present invention is at least 90%. In another embodiment, the degree of $^{15}$N-labeling of the compositions of the present invention is at least 95%. In another embodiment, the degree of $^{15}$N-labeling of the compositions of the present invention is at least 97%. In yet another embodiment, the degree of $^{15}$N-labeling of the compositions of the present invention is greater than 99%. However, the degree of labeling of the compositions of the present invention is not limited to any specific value listed herein, and can be any value as would be understood by a person skilled in the art.

The degree of $^{15}$N-labeling of the compositions produced using the methods of the present invention is primarily limited only by the degree of labeling of the $^{15}$N media in which the sample is cultured. For example, in one embodiment, the degree of $^{15}$N-labeling of the $^{15}$N-ammonium source will affect the degree of labeling in the composition of the present invention after culturing. If the degree of labeling of $^{15}$N-ammonium source used in the culture medium is less than 100%, then the degree of labeling in the composition produced will be less than 100%, i.e., substantially proportional to the degree of labeling of $^{15}$N-ammonium source. Similarly, the degree of $^{15}$N-labeling of the $^{15}$N-glutamine can also affect the degree of labeling in the composition after culturing.

The present invention provides methods for identifying and/or quantifying a glycan in a sample through the use of a $^{15}$N-labeled glycan or glycoconjugate standard. Referring to FIG. 1, one embodiment of the method 100 of identifying and/or quantifying one or more glycans of the present invention generally comprises the following steps. A previously prepared $^{15}$N-labeled standard glycoprotein is prepared according to the methods of standard preparation of the present invention described herein 105. The $^{15}$N-labeled standard glycoprotein is mixed with a sample comprising one or more glycoproteins 110. In one embodiment, the $^{15}$N-labeled standard glycoprotein is a $^{15}$N-labeled glycoprotein in a $^{15}$N-labeled monoclonal antibody ($^{15}$N mAb). Further, the sample can comprise any glycoconjugate from any cell or tissue, such as, but not limited to, an antibody, monoclonal antibody (mAb), a hormone, cytokine, clotting factor, fusion protein, enzyme, or enzyme inhibitor, or antiserum.

It is critical to monitor and characterize the glycosylation profile of any therapeutic protein to ensure that a protein to be administered to a patient matches the proper profile and composition. MAbs are a particularly important application for the methods and compositions of the present invention because of the large number of mAb-based treatments currently being developed. The methods of the present invention can be used to accurately confirm the proper glycosylation profile of a mAb, or any other protein, to ensure that a mAb batch produced for therapeutic purposes is of the proper composition and quality.

Once the standard and sample are mixed, the glycoproteins can be directly analyzed, or can be fragmented into glycopeptides 120. Glycopeptides in the sample can be analyzed, or the glycans can be released from either glycoproteins, or from glycopeptide mixtures 130. The glycans can then be analyzed 140 by any method known to a person skilled in the art. For example, the glycans can be analyzed directly by MS, by comparing the ratio of the peak height or peak area of one or more $^{14}$N glycans to the corresponding one or more $^{15}$N glycans. In one embodiment, the glycans can be derivatized after release, but before MS analysis. In one embodiment, the MS analysis can be by MALDI, ESI or LC-MS.

In one embodiment, an equal or substantially equal amount of the same reference standard can be added to more than one sample to be tested, and the ratio of one or more glycans of interest obtained for one sample can be directly compared to the ratio obtained from at least one other sample. For example, in one such embodiment, an application of the method of the present invention can be used for batch-to-batch quality assurance and quality control (QA/QC) of mAbs or other types of biopharmaceuticals, where a standard $^{15}$N mAb or biopharmaceutical is used for the analysis and comparison of multiple batches.

Figure 2:
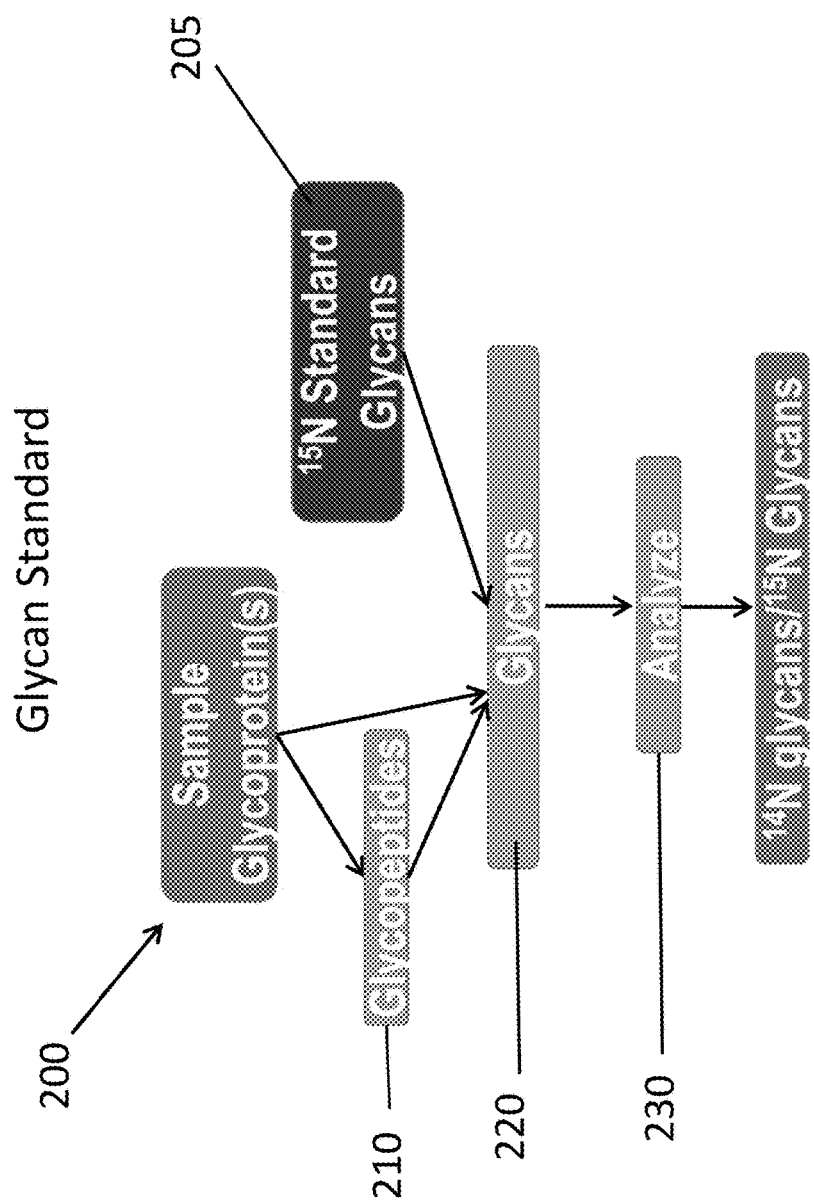
FIG. 2 is a schematic diagram of an exemplary embodiment of the method of the present invention for identifying and/or quantifying glycans, using a $^{15}$N-labeled glycans as a reference standard.

Referring now to FIG. 2, another embodiment of a method for identifying and/or quantifying one or more glycans is shown. In this embodiment, the method 200 of the present invention uses glycans for a standard instead of glycoproteins. In such an embodiment, the glycan analytical standard is prepared as described herein 205. One or more sample glycoproteins are fragmented into glycopeptides 210. Sample glycans are then released from the glycopeptides and mixed with the $^{15}$N standard glycans 220. Alternatively, the glycans can be released directly from the glycoproteins. The glycans can then be analyzed 230 by the same methods used to analyze glycans previously described herein for the method shown in FIG. 1.

In a preferred embodiment of the method of the present invention, the amount of sample glycans or glycoconjugates in each sample, and the amount of $^{15}$N-labeled standard added to each sample is substantially the same. However, the concentrations and/or volumes of the sample glycoproteins and/or standards used in the methods of the present invention can be different, as long as they are known.

While it is contemplated that an analytical standard produced using the methods of the present invention can be used in the analysis of a sample with most or all of the same glycans as the standard, a $^{15}$N standard of the present invention can also be used as a standard for the analysis of any other material with N-linked glycans. For example, a mAb reference standard can be used as an internal standard for another mAb sample of the same type, where both the standard and the sample have many, if not all, of the same glycans. In addition, a $^{15}$N mAb reference standard can also be used as a standard for any other protein with N-linked glycans. Accordingly, some of the glycans in the standard may be different from the glycans in the sample.

The compositions of the present invention for a standard may also include other materials aside from $^{15}$N-labeled glycans or glycoconjugates, i.e., the $^{15}$N-labeled glycans or glycoconjugates do not need to be isolated to be used as a standard. In addition to glycoproteins, many other glycoconjugates can be similarly analyzed, for example glycolipids and proteoglycans, and the like. In one embodiment, the standard of the present invention can comprise the growth medium. In another embodiment, the standard of the present invention can comprise cells, tissue, extracellular material, and/or any other material present in the growth medium used to produce the $^{15}$N-labeled glycans or glycoconjugates via the method of the present invention.

In one embodiment, the method of the present invention is a method for determining the effect of a modulator on a sample. In such an embodiment, a determination of any changes to the glycans or glycoconjugates in the sample is used to determine the effect of a modulator on the sample. For example, the sample can be modulated by means of exposing the sample to a compound of interest, for example a drug, protein, microbe, or suspected toxin; exposing the sample to a change in an environmental condition; or exposing the sample to radiation. However, the modulator applied to the sample can be any form of modulation, perturbation, manipulation, and the like, as would be understood by a person skilled in the art. In such a method, the glycans of a control sample and a modulated sample can be compared using the method of identifying and/or quantifying glycans described herein.

Further, the methods of the present invention further include using a $^{15}$N-ammonia source in conjunction with any method described in Wells et al. (U.S. Patent App. Pub. No. 2010/0297609). Accordingly, the present invention relates to the discovery that the addition of a $^{15}$N-ammonia source to the IDAWG method or any other method described in Wells provides a substantial improvement in the accuracy of those methods.

The medium used in the methods of the present invention is preferably a serum-free medium, i.e., free of IgG, animal protein, fetal calf serum, and the like. Accordingly, the serum-free medium will be substantially free of any glutamine other than the isotopically-labeled glutamine added.

The methods of the present invention can be used to label and/or analyze any therapeutic glycoprotein. Examples of glycoproteins that can be labeled and/or analyzed using the methods and compositions of the present invention include, but are not limited to: monoclonal antibodies, such as tocilizumab, bevacizumab, alemtuzumab, trastuzumab, adalimumab, denosumab, rituximab, golimumab, panitumumab, omalizumab, ipilimumab, ibritumomab tiuxetan, tositumomab-I131, muromonab-CD3, eculizumab ofatumumab, belimumab, gemtuzumab ozogamicin, palivizumab, cetuximab, canakinumab, infliximab, abciximab, basiliximab, and daclizumab; fusion proteins, such as alefacept, rilonacept, etanercept, belatacept, and abatacept; hormones, such as follitropin-β, follitropin-alpha, choriogonadotropin α, thyrotropin α, and somatropin; cytokines, such as darbepoetin α, erythropoietin (EPO), interferon β-1a; clotting factors, such as antihemophilic factor; enzyme or enzyme inhibitors, such as antithrombin, alteplase, laronidase, imiglucerase, human DNase, pancrelipase, and hyaluronidase; and antisera, such as antithymocyte globulin, crotalidae polyvalent immune Fab, and digoxin immune Fab (Ghaderi et al., 2012, Biotech. and Genetic Eng. Rev. 28, 147-176).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compositions of the present invention and practice the claimed methods. The following working examples therefore, specifically point out the preferred embodiments of the present invention, and are not to be construed as limiting in any way the remainder of the disclosure.

Example 1

Isotopically Labeling a Glycoprotein with $^{15}$N Glutamine and $^{15}$N Ammonium Chloride An in vivo approach was used to produce glycans/glycoconjugates whose glycans are labeled with $^{15}$N by the addition of $^{15}$N labeled glutamine and $^{15}$N labeled ammonium chloride to the media, to produce a monoclonal antibody (mAb) whose glycans have been isotopically labeled. The labeled mAb was used as an internal standard for the analysis of glycans on human Abs isolated from serum. The error in the resulting analytical measurements was over 10 times smaller than current best practices. In addition to compensating for variable instrument response, this improvement also results from adding the standard mAb to the serum sample before any sample processing has occurred, and therefore provides correction for the glycan losses resulting from sample handling/processing/etc.

This method can be used for recombinant proteins, glycoproteins, extracellular matrix glycans, and native glycans, or glycans after they are released from various glycoconjugates.

Protocol for Producing Labeled Glycoproteins in Cells.

Cells were adapted to isotopically labeled media to ensure high isotopic incorporations. Here, cells are transferred into serum free media containing the $^{15}$N species, and allowed to grow. Three (3) passages were used, which provided good isotope incorporation for the cells investigated, however, the number of passages has not been optimized, and any number of passages can be used, as would be understood by a person skilled in the art.

Cells were grown using Gln-free medium, i.e., free of IgG, animal protein, fetal calf serum, etc. Life Technologies CD Hybridoma medium is an example of a medium that works well for this application. The media is supplemented with amide-$^{15}$N-Gln, and is supplemented with $^{15}$N Ammonium chloride (a concentration of 10 mM was used, but this has not been optimized). Cells were then grown using standard procedures for cell growth, as would be understood by a person skilled in the art.

Figure 3:
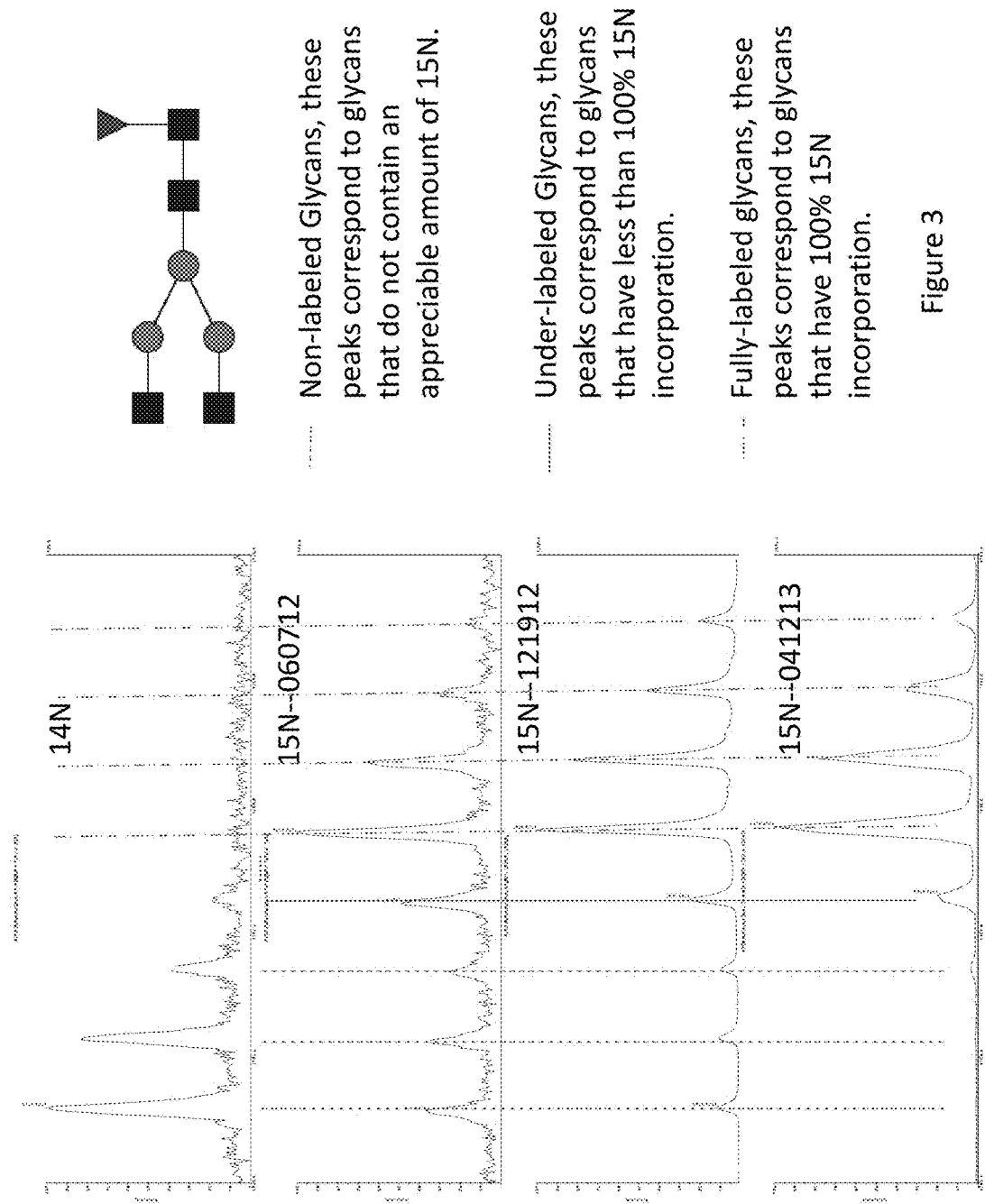
FIG. 3 is a set of mass spectra for analysis of a specific glycan in a sample, wherein the spectrum titled "14N" is for an unlabeled glycan; the spectra titled "15N-060712" and "15N-121912" are for a $^{15}$N-labeled glycan labeled via the IDAWG method known in the art; and the spectrum titled "15N-041213" is for a $^{15}$N-labeled glycan labeled using one embodiment of the method of the present invention.
Figure 4:
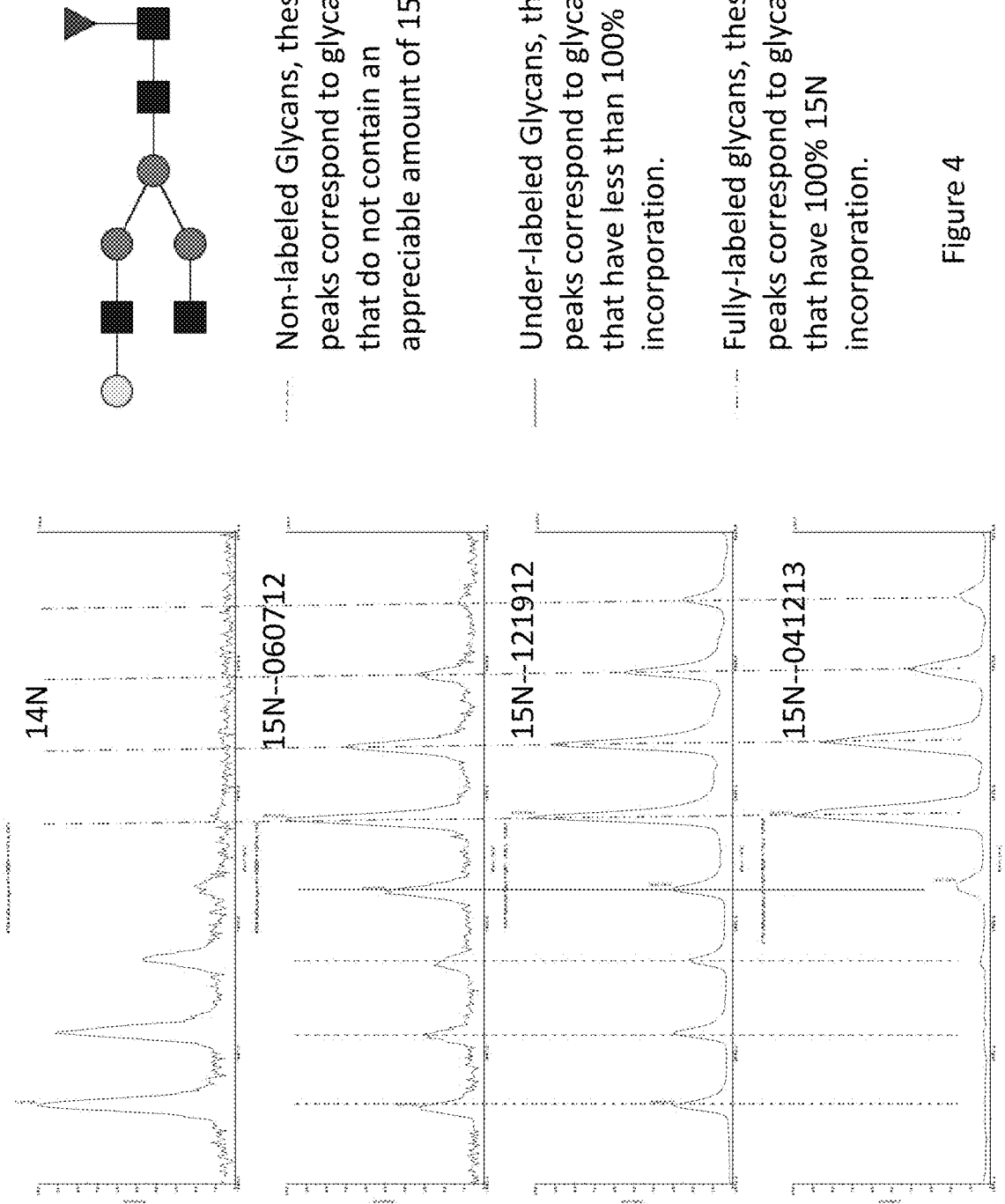
FIG. 4 is a set of mass spectra for analysis of another specific glycan in a sample, wherein the spectrum titled "14N" is for an unlabeled glycan; the spectra titled "15N-060712" and "15N-121912" are for a $^{15}$N-labeled glycan labeled via the IDAWG method known in the art; and the spectrum titled "15N-041213" is for a $^{15}$N-labeled glycan labeled using one embodiment of the method of the present invention.
Figure 5:
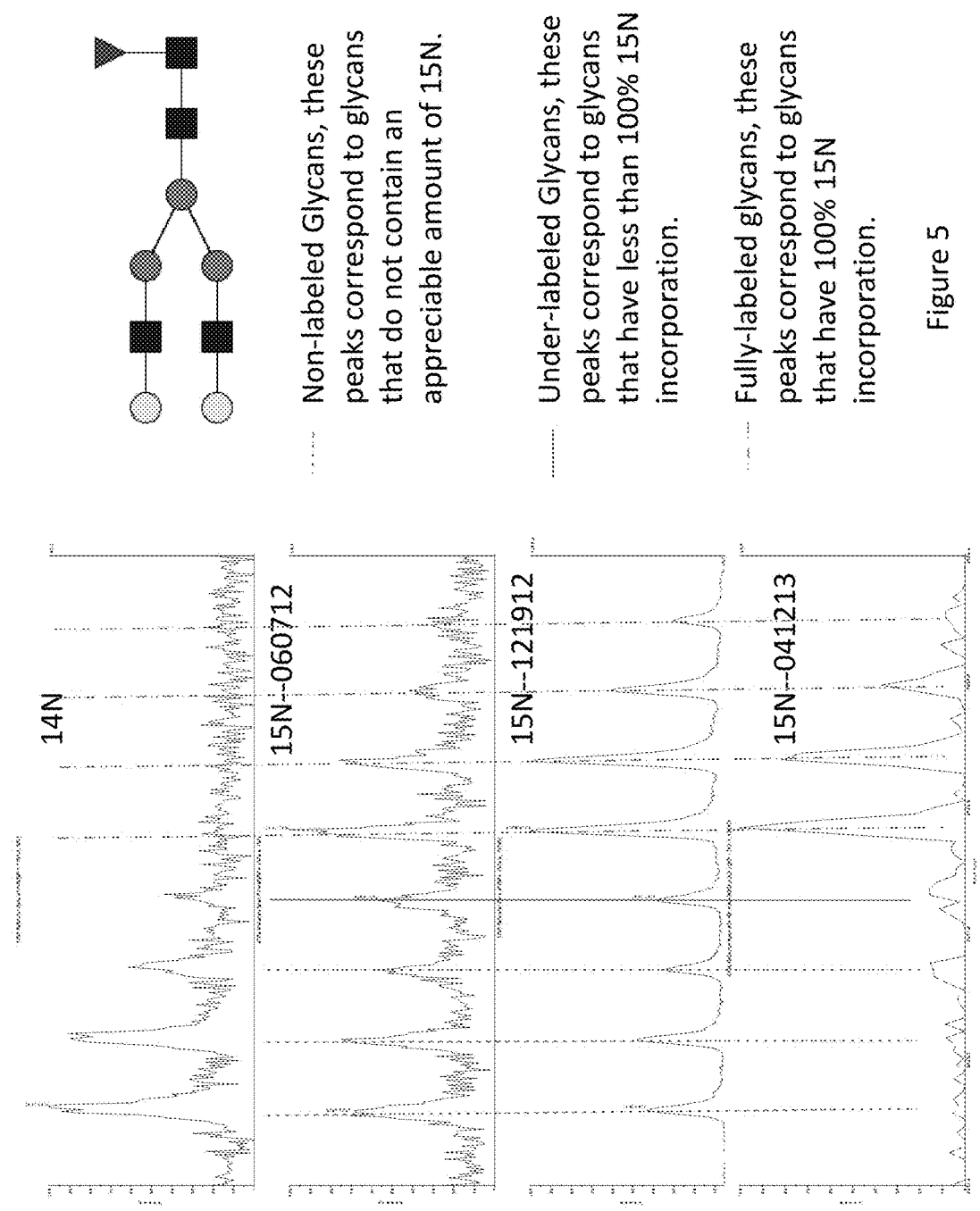
FIG. 5 is a set of mass spectra for analysis of yet another specific glycan in a sample, wherein the spectrum titled "14N" is for an unlabeled glycan; the spectra titled "15N-060712" and "15N-121912" are for a $^{15}$N-labeled glycan labeled via the IDAWG method known in the art; and the spectrum titled "15N-041213" is for a $^{15}$N-labeled glycan labeled using one embodiment of the method of the present invention.

The MALDI spectra shown in FIGS. 3, 4, and 5 show the intensity of the various isotopic peaks for the 3 dominant glycans present in the cells investigated (G0F, G1F, and G2F in FIGS. 3, 4, and 5, respectively). The top spectrum in each of FIGS. 3, 4, and 5 is for the glycans grown in $^{14}$N media and is included as a reference.

The middle 2 spectra in FIGS. 3-5, labeled as "15N-060712" and "15N-121912" in each figure, are glycans released form mAbs grown using only amide-$^{15}$N-Gln per the IDAWG method. This media contained animal proteins and was not supplemented with $^{15}$N ammonium chloride. These glycans display 3 sets of isotopic variants: 1) low mass variants which do not appear to contain substantial amounts of $^{15}$N (dashed line), 2) a peak corresponding to under-labeling of $^{15}$N, e.g., 3 of the 4 nitrogens are $^{15}$N (solid lines), and 3) peaks that correspond to glycans with four $^{15}$Ns incorporated, i.e., the maximum number, (dot-dashed lines). Note that the relative amount of the non-labeled glycans does not decrease substantially between these 2 samples in each of FIGS. 3-5, even though the glycans in the "15N-121912" samples in each figure were obtained from cells that had been in the amide-$^{15}$N-Gln media for approximately 6 months longer than the "15N-060712" sample. These spectra indicate that something other than $^{15}$N-Gln media, or in addition to $^{15}$N-Gln media, is needed to increase the degree of isotopic labeling in these samples, as there is a large population of glycans that are not isotopically labeled. In other words, the IDAWG approach does not appear to be capable of producing the labeled glycans in sufficient isotopic purity to be useful in most applications.

The bottom spectra in FIGS. 3-5, i.e., the spectra labeled "15N-041213," were obtained from glycans released from a mAb grown using one embodiment of the method of the present invention. Cells were grown using Gln-free medium, that is medium free of IgG, animal protein, fetal calf serum, etc., and supplemented with both amide-$^{15}$N-Gln and $^{15}$N Ammonium chloride. Here the peaks corresponding to non-labeled glycans almost completely disappeared. There is still a peak that corresponds to an under-labeled glycan. The ratio of the under-labeled peak is about 10%, which corresponds approximately to the $^{15}$N isotopic purity in the starting reagents (amide-$^{15}$N-Gln and $^{15}$N Ammonium chloride). In other words, the degree of isotopic labeling in the starting reagents was approximately 90%. These spectra indicate that the method of the present invention is capable of producing glycans with the uniform isotopic labeling needed for use as standards.

Results Using $^{15}$N MAb to Quantitate Glycans on Serum IgGs.

Human IgGs were purified from serum using a protein G column. Samples were then made so that the $^{14}$N IgG to $^{15}$N mAb ratios (protein ratios determined by Bradford assay) were 1:5, 1:2, 2:1, and 5:1. These samples were analyzed (glycans released, tagged, analyzed by LC-MS/MS) in triplicate. The average percent error for each solution was found to be: 4% for the 1:5 protein ratio, 1% for the 1:2 ratio, 9% for the 2:1 ratio, and 9% for the 5:1 ratio. The samples were also analyzed without the $^{15}$N-mAb reference and the average percent error at each concentration was found to be 36% for the 1:5 ratio, 8% for the 1:2 ratio, 35% for the 2:1 ratio, and 96% for the 5:1 ratio. Therefore, the use of the $^{15}$N standard of the present invention improved the precision and accuracy.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method for making a standard for the quantification or identification of glycans in a sample, comprising the steps of:
   culturing a sample in a culture medium, wherein said culture medium comprises $^{15}$N-glutamine and a $^{15}$N-ammonium source; and
   selectively incorporating $^{15}$N isotope into an activated sugar, thereby producing $^{15}$N-labeled glycoconjugates and/or $^{15}$N-labeled glycans;
   wherein the $^{15}$N-labeled glycoconjugates and/or $^{15}$N-labeled glycans form a standard for the quantification or identification of glycans in a sample.

2. The method of claim 1, further comprising the step of isolating at least one $^{15}$N-labeled glycoconjugate or glycan from said culture medium.

3. The method of claim 1, further comprising the step of releasing at least one $^{15}$N-labeled glycan from said at least one $^{15}$N-labeled glycoconjugate.

4. The method of claim 1, wherein said $^{15}$N-labeled glycoconjugate is a $^{15}$N-labeled glycoprotein, $^{15}$N-labeled glycolipid, or $^{15}$N-labeled proteoglycan.

5. The method of claim 1, wherein said $^{15}$N-labeled glycoconjugate is selected from the group consisting of a $^{15}$N-labeled monoclonal antibody (mAb), fusion protein, hormone, cytokine, clotting factor, enzyme inhibitor, and enzyme.

6. The method of claim 5, wherein said $^{15}$N-labeled glycan is attached to erythropoietin (EPO).

7. The method of claim 1, wherein said $^{15}$N-ammonium source is $^{15}$N-ammonium chloride.

8. The method of claim 1, wherein said culture medium is a serum-free medium.

9. The method of claim 1, wherein the degree of labeling of said at least one glycan of the $^{15}$N-labeled glycoconjugate or $^{15}$N-labeled glycan is in the range of about 80-100%.

10. The method of claim 1, wherein the degree of labeling of said at least one glycan of the $^{15}$N-labeled glycoconjugate or $^{15}$N-labeled glycan is at least 90%.

11. The method of claim 1, wherein the degree of labeling of said at least one glycan of the $^{15}$N-labeled glycoconjugate or $^{15}$N-labeled glycan is at least 95%.

* * * * *